United States Patent [19]
Stossel

[11] Patent Number: 6,015,437
[45] Date of Patent: Jan. 18, 2000

[54] SHOULDER PROSTHESIS

[75] Inventor: Clifford Alain Stossel, Kent, United Kingdom

[73] Assignee: Headcorn Instrumentation Ltd., Kent, United Kingdom

[21] Appl. No.: 09/062,739

[22] Filed: Apr. 20, 1998

[30] Foreign Application Priority Data

Apr. 18, 1997 [GB] United Kingdom .................. 9707853

[51] Int. Cl.⁷ ...................................................... A61F 2/40
[52] U.S. Cl. ............................................................ 623/19
[58] Field of Search ................... 623/18, 19, 22, 623/23

[56] References Cited

U.S. PATENT DOCUMENTS

| | | | |
|---|---|---|---|
| 3,906,550 | 9/1975 | Rostoker et al. | 623/18 |
| 4,279,041 | 7/1981 | Buchholz . | |
| 4,355,427 | 10/1982 | Schneider . | |
| 4,770,661 | 9/1988 | Oh | 623/18 |
| 4,936,855 | 6/1990 | Sherman | 623/18 |
| 5,015,257 | 5/1991 | Crowninshield et al. | 623/18 |
| 5,108,441 | 4/1992 | McDowell | 623/19 |
| 5,383,936 | 1/1995 | Kubein-Meesenburg et al. | 623/19 |
| 5,405,403 | 4/1995 | Mikhail | 623/19 |
| 5,507,833 | 4/1996 | Bohn | 623/23 |

FOREIGN PATENT DOCUMENTS

| | | | |
|---|---|---|---|
| 24442 | 3/1981 | European Pat. Off. | 623/19 |
| 0 339 530 | 11/1989 | European Pat. Off. . | |
| 0 622 062 | 11/1994 | European Pat. Off. . | |
| 639359 | 2/1995 | European Pat. Off. | 623/19 |
| 2 664 809 | 1/1992 | France . | |
| 44 45 892 A1 | 6/1996 | Germany . | |
| 2 210 793 | 6/1989 | United Kingdom . | |
| 2223172 | 4/1990 | United Kingdom | 623/19 |
| WO 95/22302 | 8/1995 | WIPO . | |
| WO 96/41597 | 12/1996 | WIPO . | |

*Primary Examiner*—Jeffrey A. Smith
*Assistant Examiner*—Eduardo C. Robert
*Attorney, Agent, or Firm*—Oliff & Berridge, PLC

[57] ABSTRACT

A shoulder prosthesis includes a shaft and, at the head of the shaft, a member having a surface that is hemispherical and extends continuously beyond the base of the hemisphere with a smaller radius to provide, in use, at least 210° of total rotation.

6 Claims, 1 Drawing Sheet

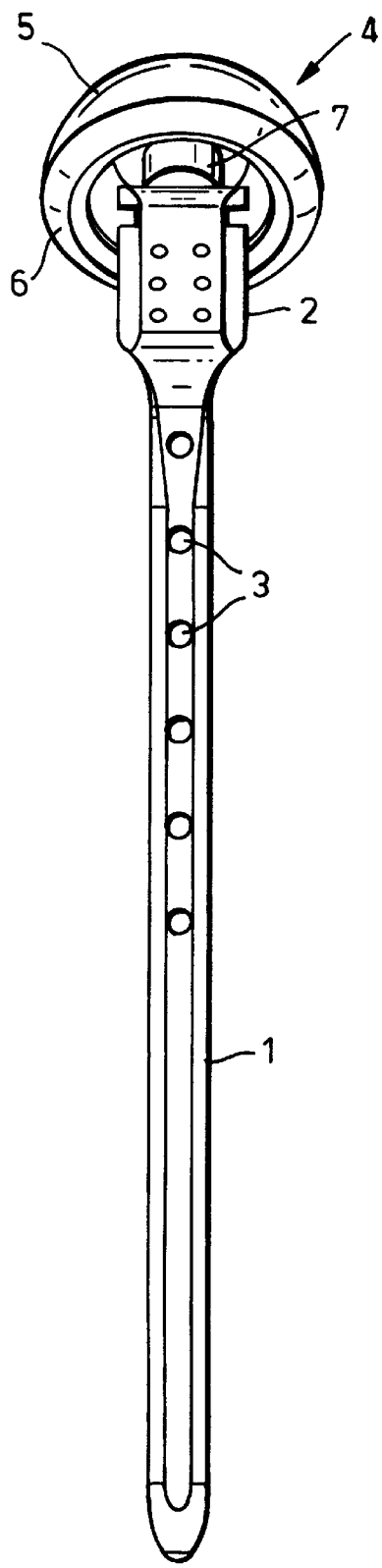
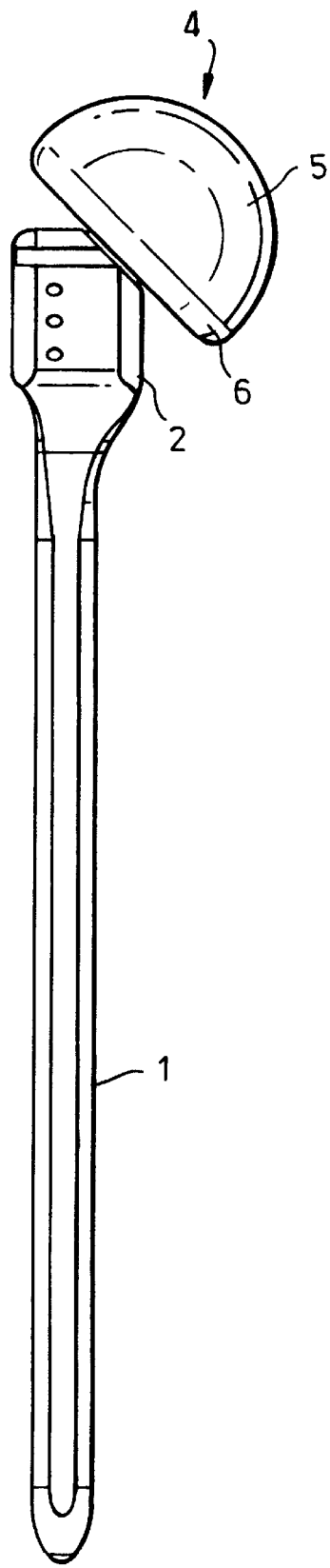

SHOULDER PROSTHESIS

FIELD OF THE INVENTION

This invention relates to a prosthesis, in particular for the shoulder.

BACKGROUND OF THE INVENTION

In about 1969, when shoulder replacements using the Neer type of prosthesis were coming into widespread use, the humeral head was an integral part of the prosthesis. As shoulder replacement became more widely used, modular systems were introduced. Humeral heads of different sizes were available, with plastic trial shapes, to ensure that the best size was chosen.

Available information reports that normal movements of the shoulder showed a range of 90° internal rotation to 90° of external rotation, i.e. a total range of 180°. Accordingly, known humeral head prostheses, such as those described above, were based on a hemisphere. This appeared to be close to the anatomical shape, and was therefore entirely suitable. However, the long head of the biceps muscle which passes over the anterior aspect of the shoulder impinges against the angular shape of a hemispherical humeral head. This causes pain and fraying of the tendon.

SUMMARY OF THE INVENTION

This invention is based at least in part on measurements of actual shoulder movements which showed that, if it is intended to reach the back of the opposite shoulder, the arm is flexed at the shoulder joint and that, with this flexion, a further 30° of internal rotation is required beyond the conventional range. This makes a total rotation of 210°. These measurements help to explain why known protheoes are unsatisfactory, in that there is the disadvantage that the humeral head prosthesis rests on its edge against the glenoid, where it can become locked against a rough portion or itself damage the articular cartilage.

According to the present invention, a shoulder prosthesis comprises a shaft and a head, and the head comprises a continuous surface allowing for at least 210° of total rotation. Thus, the present invention allows the prosthesis to be fixed to the humerus, in a position 30° backwards from the coronal to anatomical position, and to rotate fully within the glanoid.

DESCRIPTION OF THE DRAWINGS

In the accompanying drawings, FIGS. 1A and 1B are respective mutually-orthogonal side views of a prosthesis that is a preferred embodiment of the present invention.

DESCRIPTION OF THE INVENTION

The invention will now be described by way of example only with respect to the accompanying drawings. FIGS. 1A and 1B show a prosthesis that comprises a shaft 1 having a head 2 and, positioned at intervals along the shaft, fixation holes 3. The holes 3 are suitable for fixing the prosthesis to the patient's humerus. On the head 2 of the shaft 1, a member generally indicated at 4 is mounted.

The member 4 comprises a hemispherical part 5 and a base part 6 that provides a smooth surface continuous with the surface of the hemisphere. This extended surface is itself generally part-spherical or part of an annulus. It provides a surface extending for at least 30° beyond the 180° provided by the hemisphere.

The member 4 is offset with respect to the longitudinal axis of the shaft. The offset angle (between the two dashed lined shown in FIG. 1B) may be 30° to 60°, and is preferably about 45°, but this angle is not critical, provided that the surface of the member allows the rotation of at least 210°, and preferably at least 270°. The hemispherical member is conveniently fixed to the head by means of co-operating male and female parts.

The illustrated design provides a surface extending essentially through a total of 360°, with the extension beyond the hemisphere being of a smaller radius. This leaves a central aperture, within which a stem 7 is mounted. This item fits into a corresponding recess in the top of the shaft.

The illustrated head gives continuous full articulation with the structures of the scapula throughout the fullest possible range of anatomical movement. Tests have shown that, in the fullest internal rotation, the centre of the axis of the huimeral head actually points laterally. Because of the unique shape of the illustrated head, there is still a full articulation with the glenoid in this fully internally rotated position.

The completeness of the head means that in the other quadrant and plane, simultaneously the long head of biceps tendon is in its natural course.

I claim:

1. A shoulder prosthesis comprising a shaft and, at a head of the shaft, a member having a surface that is hemispherical and extends continuously beyond a base of the hemisphere with a smaller radius to provide, in use, at least 210° of total rotation.

2. A prosthesis according to claim 1, wherein the angle of total rotation that is provided is at least 270°.

3. A prosthesis according to claim 1, wherein the angle of total rotation that is provided is essentially 360°.

4. A prosthesis according to claim 1, wherein the continuous extension is essentially annular.

5. A prosthesis according to claim 4, wherein the member defines an aperture within which means for fixing the member to the shaft is provided.

6. A prosthesis according to claim 1, wherein an axis of symmetry of the member and a longitudinal axis of the shaft are offset by about 45°.

* * * * *